(12) United States Patent
Aramaki et al.

(10) Patent No.: US 10,132,432 B2
(45) Date of Patent: Nov. 20, 2018

(54) FERRULE COUPLING AND SEALING MECHANISM FOR LIQUID PASSAGE NOZZLE OF MEMBRANE MODULE

(71) Applicant: ASAHI KASEI MEDICAL CO., LTD., Tokyo (JP)

(72) Inventors: Shosaku Aramaki, Tokyo (JP); Tomohiro Saotome, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 531 days.

(21) Appl. No.: 14/758,678

(22) PCT Filed: Jan. 9, 2014

(86) PCT No.: PCT/JP2014/050243
§ 371 (c)(1),
(2) Date: Jun. 30, 2015

(87) PCT Pub. No.: WO2014/109367
PCT Pub. Date: Jul. 17, 2014

(65) Prior Publication Data
US 2015/0362099 A1 Dec. 17, 2015

(30) Foreign Application Priority Data
Jan. 11, 2013 (JP) .................................. 2013-003935

(51) Int. Cl.
*F16L 15/00* (2006.01)
*F16L 19/02* (2006.01)
(Continued)

(52) U.S. Cl.
CPC ............ *F16L 15/00* (2013.01); *A61M 39/10* (2013.01); *A61M 39/16* (2013.01); *A61M 39/20* (2013.01);
(Continued)

(58) Field of Classification Search
CPC ..... F16L 19/0231; F16L 15/00; F16L 19/025; F16L 21/06; F16L 2201/44; F16L 23/036;
(Continued)

(56) References Cited

U.S. PATENT DOCUMENTS 919,913 A * 4/1909 Miller .......................... 285/384
3,001,802 A 9/1961 Rebman
(Continued)

FOREIGN PATENT DOCUMENTS

EP 0 200 254 11/1986
JP 6-241362 8/1994
(Continued)

OTHER PUBLICATIONS

Supplementary European Search Report, dated Feb. 3, 2016 with respect to European Patent Application No. 14738073.7.
(Continued)

*Primary Examiner* — Carib A Oquendo
(74) *Attorney, Agent, or Firm* — Greenblum & Bernstein, P.L.C.

(57) ABSTRACT

A ferrule coupling is easy to mount onto members to be coupled such as pipe conduits and apparatuses and can reliably maintain the sealability even when subjected to temperature rises and falls due to a sterilization process etc. A ferrule coupling has an annular male screw member which is provided on one of members to be coupled and has a thread formed on the outer peripheral surface, and an annular female screw member which is provided on the other of the members to be coupled and has a thread formed on the inner peripheral surface. The male screw member and the female screw member are screw-engaged with each other to thereby couple the members to be coupled with each other. The male screw member has a cut section at one part
(Continued)

in the circumferential direction, and can be opened or closed such that the cut section widens or narrows.

14 Claims, 13 Drawing Sheets

(51) Int. Cl.
*F16L 19/025* (2006.01)
*A61M 39/10* (2006.01)
*A61M 39/16* (2006.01)
*A61M 39/20* (2006.01)
*F16L 23/036* (2006.01)
*F16L 55/12* (2006.01)

(52) U.S. Cl.
CPC ......... *F16L 19/025* (2013.01); *F16L 19/0231* (2013.01); *F16L 23/036* (2013.01); *F16L 55/12* (2013.01); *A61M 2039/1033* (2013.01); *F16L 2201/44* (2013.01)

(58) Field of Classification Search
CPC .. F16L 49/06; F16L 55/12; A61M 2039/1033; A61M 39/10; A61M 39/16; A61M 39/20
USPC ........... 285/39, 353, 354, 390, 419; 411/433
See application file for complete search history.

(56) References Cited

U.S. PATENT DOCUMENTS

| | | | |
|---|---|---|---|
| 3,041,088 A | 6/1962 | Brandon | |
| 3,734,547 A * | 5/1973 | Kojima | F16L 19/086 285/357 |
| 4,291,906 A | 9/1981 | Donbavand | |
| 4,923,349 A | 5/1990 | Logsdon | |
| 5,226,678 A * | 7/1993 | Petranto | F16L 19/0231 285/334.5 |
| 5,344,195 A * | 9/1994 | Parimore, Jr. | F16L 19/0231 285/340 |
| 5,775,743 A * | 7/1998 | Rochelle | F16L 19/0231 285/148.13 |
| 6,981,723 B2 * | 1/2006 | Landvik | F16L 15/006 285/390 |
| 2011/0272888 A1 | 11/2011 | Irizzary et al. | |

FOREIGN PATENT DOCUMENTS

| | | |
|---|---|---|
| JP | 2006-82026 | 3/2006 |
| JP | 2006-226303 | 3/2006 |
| JP | 2010-196732 | 9/2010 |
| JP | 2010-259992 | 11/2010 |
| WO | 2007/024144 | 3/2007 |

OTHER PUBLICATIONS

International Search Report and English language translation thereof, dated Apr. 15, 2014.
International Preliminary Report on Patentability and English language translation thereof, dated Jul. 14, 2015.

\* cited by examiner

Fig. 11

TABLE 1

| SAMPLE NO. | TEST RESULT AFTER STERILIZATION (PRESENT INVENTION) | | TEST RESULT AFTER STERILIZATION (CONVENTIONAL JOINT) | |
|---|---|---|---|---|
| | VACUUM LEAK TEST | PRESSURE TEST 100~500kPa | VACUUM LEAK TEST | PRESSURE TEST 100~500kPa |
| 1 | ○ | ○ | ○ | ○ |
| 2 | ○ | ○ | ○ | ○ |
| 3 | ○ | ○ | × | × |
| 4 | ○ | ○ | ○ | ○ |
| 5 | ○ | ○ | × | × |
| 6 | ○ | ○ | ○ | ○ |
| 7 | ○ | ○ | ○ | ○ |
| 8 | ○ | ○ | ○ | ○ |
| 9 | ○ | ○ | × | × |
| 10 | ○ | ○ | × | × |
| 11 | ○ | ○ | ○ | ○ |
| 12 | ○ | ○ | ○ | ○ |

FERRULE COUPLING AND SEALING MECHANISM FOR LIQUID PASSAGE NOZZLE OF MEMBRANE MODULE

TECHNICAL FIELD

The present invention relates to a ferrule coupling and a sealing mechanism for a liquid passage nozzle of a membrane module.

BACKGROUND ART

In the fields of medicine, pharmaceuticals, food, etc. where hygienic control is required, a so-called ferrule, which has the shape of a flange with an enlarged diameter and is highly airtight, is often used for a coupling part between pipe conduits or apparatuses which a liquid or a gas to be handled flows through. A liquid passage nozzle of a pipe conduit or an apparatus having this ferrule is coupled with another pipe conduit etc. by means of a ferrule coupling.

In a membrane module used in the medical field, a clamp joint, which can cover the outer periphery of a coupling part between a liquid passage nozzle having a ferrule and a closure member that closes the liquid passage nozzle, and fasten the coupling part with a binding band, is used as a joint for coupling the liquid passage nozzle and the closure member (see Patent Literature 1).

CITATION LIST

Patent Literature

Patent Literature 1: Japanese Patent Laid-Open No. 2006-226303

SUMMARY OF INVENTION

Technical Problem

In the fields of medicine etc. as described above, for hygienic control, pipe conduits and apparatuses are sterilized at a high temperature before use. In this case, if the clamp joint as described above is used as a joint for the coupling part between pipe conduits or apparatuses, when subjected to large temperature rises and falls during a sterilization process, the binding band undergoes elongation and its tightening loosens, so that the sealability of the coupling part lowers. Moreover, the tightening work of the binding band-type clamp joint requires practice and skills, and insufficient tightening of the clamp joint may result in lower sealability of the coupling part. Low sealability of the coupling part may impair the sterility of the pipe conduits or the apparatuses, or cause leakage or deterioration of the contents.

The present invention has been devised in view of this point, and an object of the present invention is to provide a ferrule coupling, which is easy to mount onto members to be coupled, such as pipe conduits and apparatuses, and can reliably maintain the sealability even when subjected to temperature rises and falls due to a sterilization process etc., and a sealing mechanism for a liquid passage nozzle of a membrane module.

Solution to Problem

The present invention for achieving the above object is a ferrule coupling used in the field of manufacturing of pharmaceutical and medical products or food manufacturing, the ferrule coupling including: an annular male screw member which can be fitted on one of members to be coupled and has a thread formed on the outer peripheral surface; and an annular female screw member which can be fitted on the other of the members to be coupled and has a thread formed on the inner peripheral surface, wherein the male screw member and the female screw member are screw-engaged with each other to thereby couple the members to be coupled with each other, and the male screw member has a cut section at only one part in the circumferential direction and can be opened or closed such that the cut section widens or narrows.

According to the present invention, the work of coupling members to be coupled with each other is easy and requires no practice and skills, and high sealability can be reliably maintained even when the ferrule coupling is subjected to temperature rises and falls due to a sterilization process etc.

The male screw member may be divided into a plurality of arc members, and the plurality of arc members may be connected with one another through a connection member except at the one part defining the cut section.

The female screw member may have a cut section at one part in the circumferential direction and may be able to be opened or closed such that the cut section widens or narrows, and the ferrule coupling may further include an opening regulation member which can regulate the opening of the female screw member.

The present invention according to another aspect is a ferrule coupling used in the field of manufacturing of pharmaceutical and medical products or food manufacturing, the ferrule coupling including: an annular male screw member which can be fitted on one of members to be coupled and has a thread formed on the outer peripheral surface; and an annular female screw member which can be fitted on the other of the members to be coupled and has a thread formed on the inner peripheral surface, wherein the male screw member and the female screw member are screw-engaged with each other to thereby couple the members to be coupled with each other, and the female screw member has a cut section at only one part in the circumferential direction and can be opened or closed such that the cut section widens or narrows, and the ferrule coupling further includes an opening regulation member which can regulate the opening of the female screw member.

The female screw member may be divided into a plurality of arc members, and the plurality of arc members may be connected with one another through a connection member except at the one part defining the cut section.

The connection member may have higher flexibility than the arc member.

At least one of the male screw member and the female screw member may have a handhold part which has a plurality of protrusions projecting radially outwardly.

The male screw member may have a recessed portion, in the inner peripheral surface, which houses the end of the one of the members to be coupled.

The recessed portion of the male screw member may be formed so as to match the shape of the end of the one of the members to be coupled.

The female screw member may have a recessed portion, in the inner peripheral surface, which houses the end of the other of the members to be coupled.

The recessed portion of the female screw member may be formed so as to match the shape of the end of the other of the members to be coupled.

The above ferrule couplings may couple members to be coupled, which have a flange-shaped ferrule portion at the end, with each other.

The present invention according to another aspect is a sealing mechanism for a liquid passage nozzle of a membrane module including the above-described ferrule coupling, wherein the male screw member and the female screw member of the ferrule coupling are screw-engaged with each other to thereby airtightly couple a liquid passage nozzle of a membrane module and a closure member which closes the liquid passage nozzle with each other.

The closure member may be a balloon which is airtightly coupled on the liquid passage nozzle of the membrane module and can expand and contract.

The male screw member or the female screw member provided on the balloon side may be provided with an expansion suppression member which suppresses expansion of the balloon.

Advantageous Effects of Invention

According to the present invention, the work of mounting a ferrule coupling onto members to be coupled such as pipe conduits and apparatuses can be easily performed, and the sealability can be reliably maintained even when the ferrule coupling is subjected to temperature rises and falls due to a sterilization process etc.

BRIEF DESCRIPTION OF DRAWINGS

FIG. 11 is a table showing test results of an example.

DESCRIPTION OF EMBODIMENTS

Figure 1:
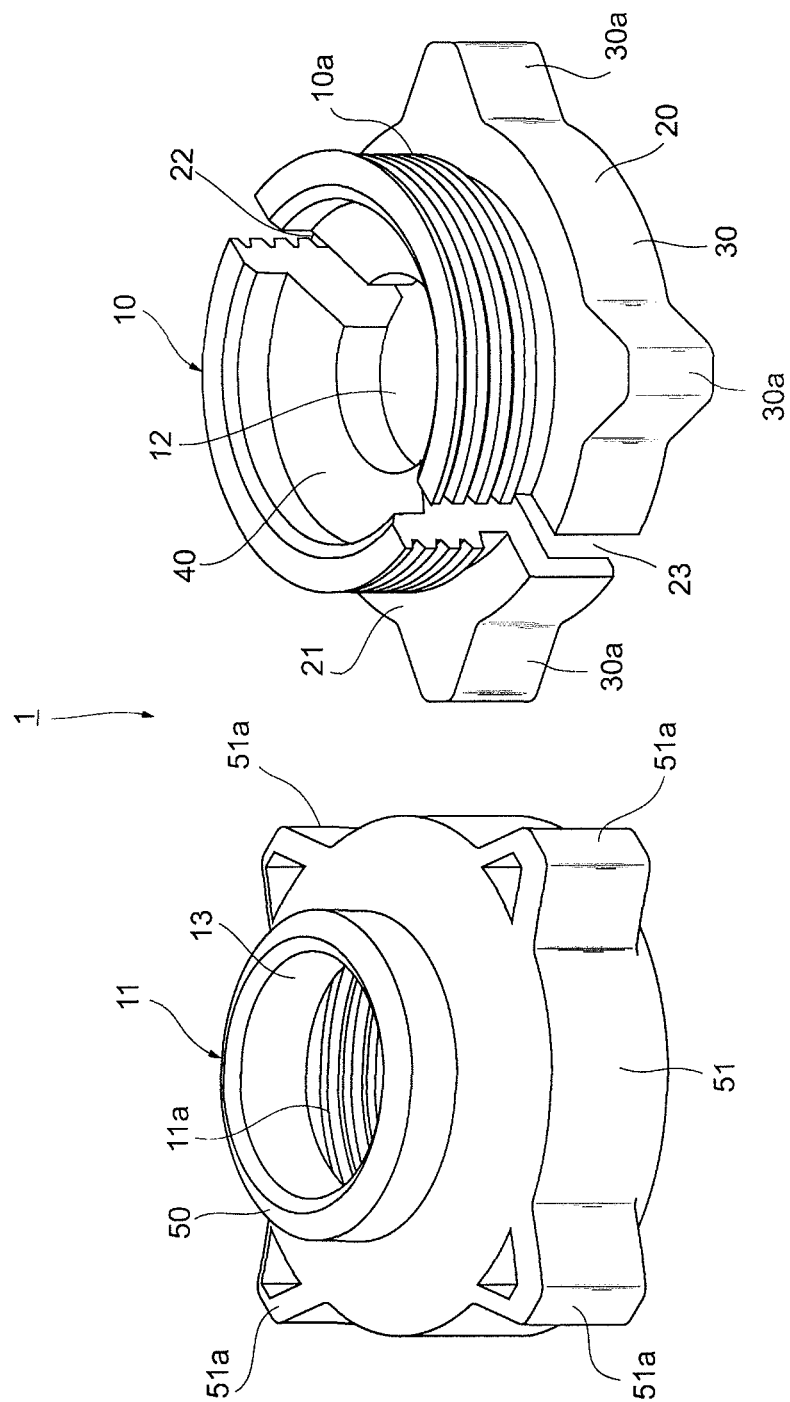
FIG. 1 is a perspective view of a ferrule coupling.

In the following, a preferred embodiment of the present invention will be described with reference to the drawings. FIG. 1 is a perspective view showing the outline of the configuration of a ferrule coupling 1 according to this embodiment. The ferrule coupling 1 is used for coupling members to be coupled such as pipe conduits with each other, at least one of which has a ferrule. The ferrule refers to a coupling part having the shape of a flange with an enlarged diameter which can highly airtightly couple members to be coupled with each other.

The ferrule coupling 1 has an annular male screw member 10 having a thread 10a formed on the outer peripheral surface, and an annular female screw member 11 having a thread 11a, which is screw-engaged with the thread 10a of the male screw member 10, on the inner peripheral surface. The male screw member 10 and the female screw member 11 have center holes 12, 13 at the center which members to be coupled such as pipe conduits pass through.

Figure 2A:
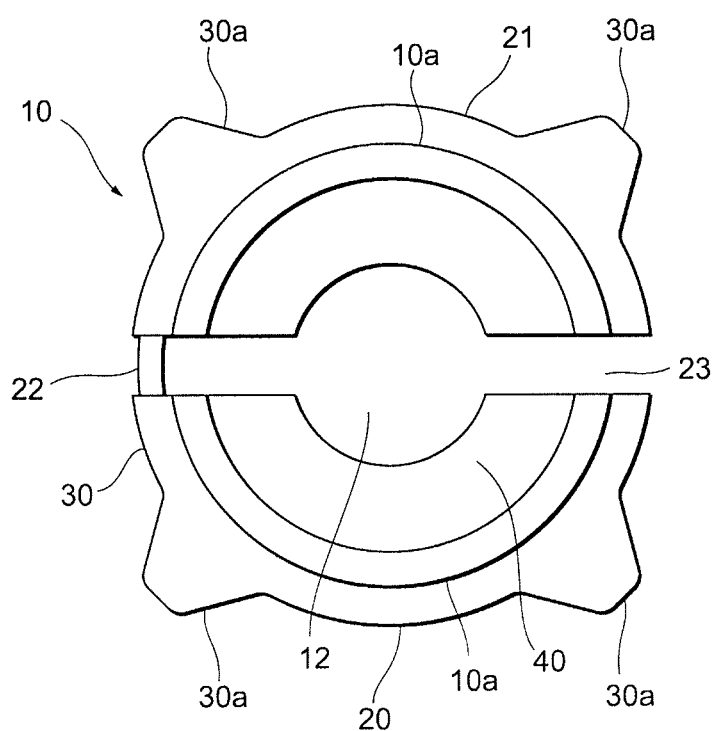
FIG. 2A is a plan view of a male screw member.
Figure 2B:
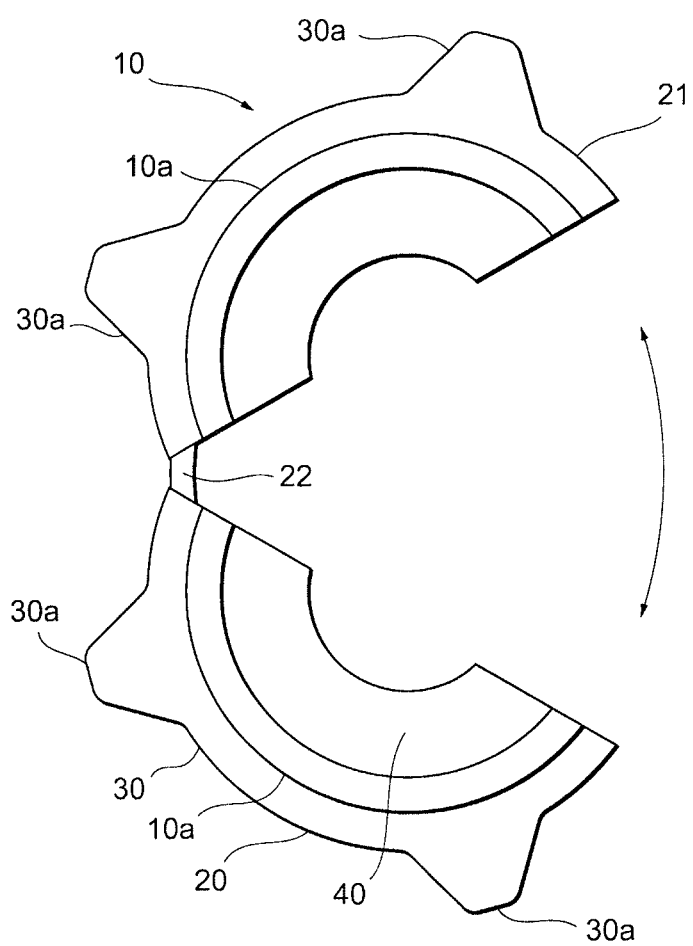
FIG. 2B is a plan view showing the male screw member in its open state.

As shown in FIG. 2A and FIG. 2B, the male screw member 10 is divided into a plurality of, for example, two arc members 20, 21. One ends in the circumferential direction of the arc members 20, 21 are connected with each other through a connection member 22, while the other ends define a cut section 23. The connection member 22 has higher flexibility than the arc members 20, 21. The connection member 22 connects, for example, outermost peripheral portions of the ends in the circumferential direction of the arc members 20, 21 with each other. The male screw member 10 is opened or closed as the cut section 23 widens or narrows with the connection member 22 serving as the fulcrum.

The male screw member 10 has a handhold part 30 which has a plurality of, for example, four protrusions 30a projecting radially outwardly.

Figure 3:
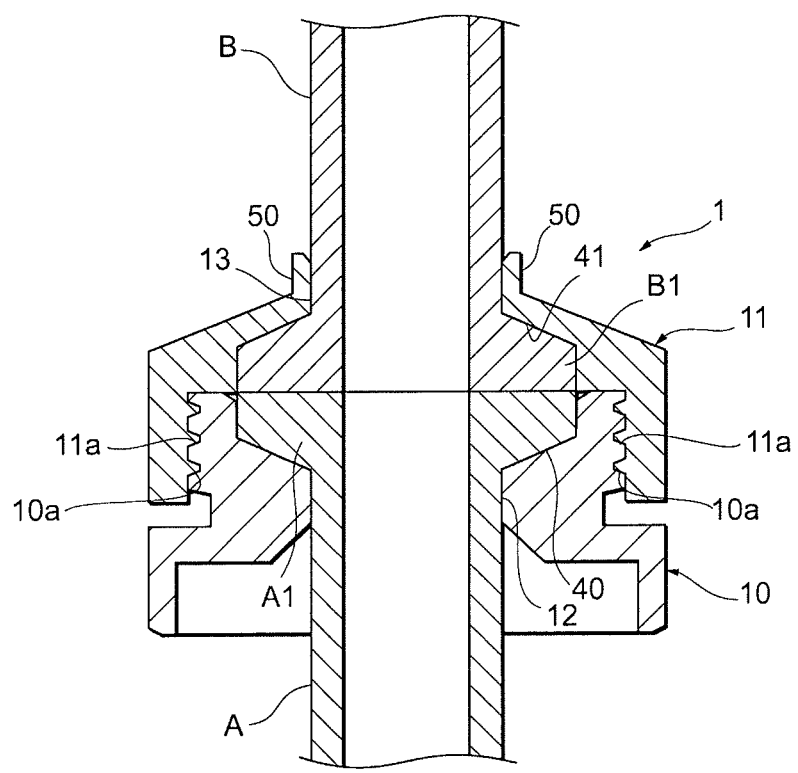
FIG. 3 is a cross-sectional view showing a state in which the ferrule coupling is mounted on members to be coupled.
Figure 10:
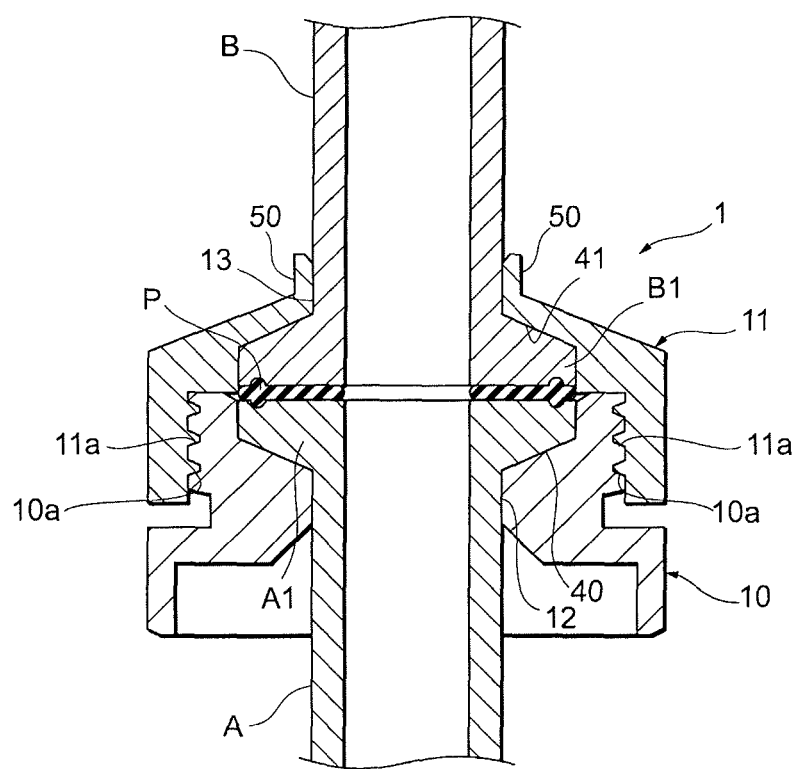
FIG. 10 is a cross-sectional view showing a state in which the ferrule coupling is mounted on ferrule portions having a packing interposed therebetween.

As shown in FIG. 3, the male screw member 10 and the female screw member 11 have recessed portions 40, 41, which house flange-shaped ferrule portions A1, B1 of the members to be coupled, in the inner peripheral surfaces of the center holes 12, 13. Here, in order to reliably maintain the sealability of the ferrule portions A1, B1 of two pipe conduits A, B to be connected with each other, the recessed portions 40, 41 of the male screw member 10 and the female screw member 11 are formed so as to match the shapes of the ferrule portions A1, B1 and to be fitted on the ferrule portions A1, B1 when the recessed portions 40, 41 hold the ferrule portions A1, B1 from upper and lower sides. As shown in FIG. 10, for example, a rubber packing P may be inserted between the ferrule portions A1 and B1.

An annular ridge portion 50 projecting to the outside is formed on the inner periphery of the surface of the female screw member 11 opposite to the male screw member 10. As shown in FIG. 1, the female screw member 11 has a plurality of, for example, four protrusions 51a, which projects to the outside, on the side peripheral surface, and the side peripheral surface serves as a handhold part 51.

The male screw member 10 and the female screw member 11 are made of a resin, for example, polyethylene, polypropylene, or polystyrene, and are each molded integrally. The material of the male screw member 10 and the female screw member 11 is not particularly limited, and they may be made of metal such as stainless steel other than a resin. Both the male screw member 10 and the female screw member 11 are not limited to being molded integrally, and may be formed by combining the parts.

To use the ferrule coupling 1, for example, as shown in FIG. 3, the male screw member 10 is mounted on the pipe conduit A having the ferrule portion A1 as one of members to be coupled, while the female screw member 11 is mounted on the pipe conduit B having the ferrule portion B1 as the other of the members to be coupled. In this case, the male screw member 10 is mounted on the pipe conduit A by being opened on the cut section 23 side as shown in FIG. 2B and holding the pipe conduit A in this state from a lateral side. Then, the male screw member 10 provided on the pipe conduit A side and the female screw member 11 provided on the pipe conduit B side are screw-engaged with each other to thereby airtightly couple the pipe conduit A and the pipe conduit B with each other.

Figure 4:
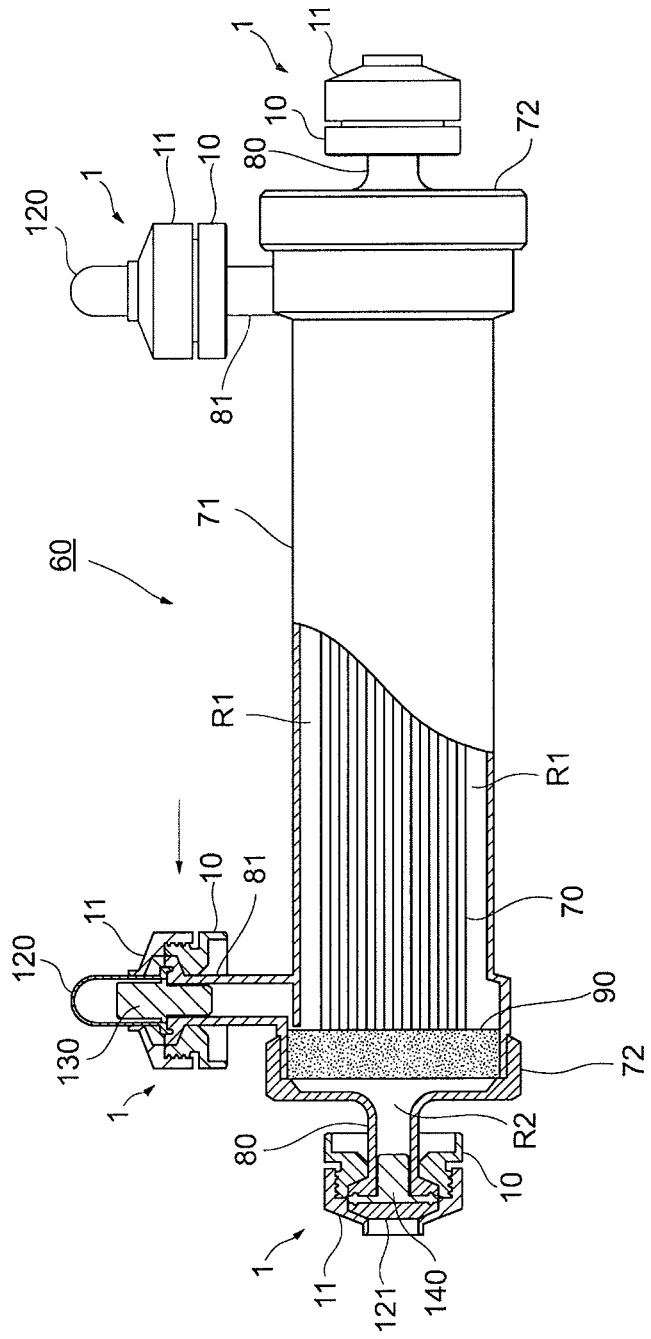
FIG. 4 is a view of the configuration of a membrane module.

Next, an example will be described in which the above-described ferrule coupling 1 is used in a sealing structure for a liquid passage nozzle of a membrane module. FIG. 4 is a partially cross-sectional view showing the outline of the configuration of a membrane module 60.

For example, as shown in FIG. 4, the membrane module 60 has a circular cylindrical module main body 71 in which a hollow fiber membrane 70 is housed in the longitudinal direction, and headers 72 covering both ends in the longitudinal direction of the module main body 71. Each header 72 is provided with a primary liquid passage nozzle 80 leading to the primary side of the hollow fiber membrane 70. On the outer peripheral-side surface of the module main body 71, two secondary liquid passage nozzles 81 leading to the secondary side of the hollow fiber membrane 70 are formed.

Both ends of the hollow fiber membrane 70 are fixed on the inner wall surface of the module main body 71 by a potting agent 90. Due to this potting agent 90, an outer peripheral space R1, which is located on the outer periphery of the hollow fiber membrane 70, and end spaces R2, which are both ends of the hollow fiber membrane 70 and which open ends of the hollow fiber membrane 70 lead to, are formed on the inside of the module main body 71. The secondary liquid passage nozzles 81 are open to the outer peripheral space R1 of the hollow fiber membrane 70, and the primary liquid passage nozzles 80 are open to the end spaces R2 of the hollow fiber membrane 70. Due to this configuration, during liquid processing of the membrane module 60, for example, a process liquid flows from one primary liquid passage nozzle 80 into one end space R2, flows out to the other end space R2 through the inside of the tube of the hollow fiber membrane 70, and flows out of the other primary liquid passage nozzle 80. The process liquid, which has passed through side wall holes of the hollow fiber membrane 70 while passing through the hollow fiber membrane 70, flows out to the outer peripheral space R1 and is discharged from the secondary liquid passage nozzles 81. While the process liquid is passing through the side wall holes of the hollow fiber membrane 70, for example, a specific substance is separated from the process liquid.

Figure 5:
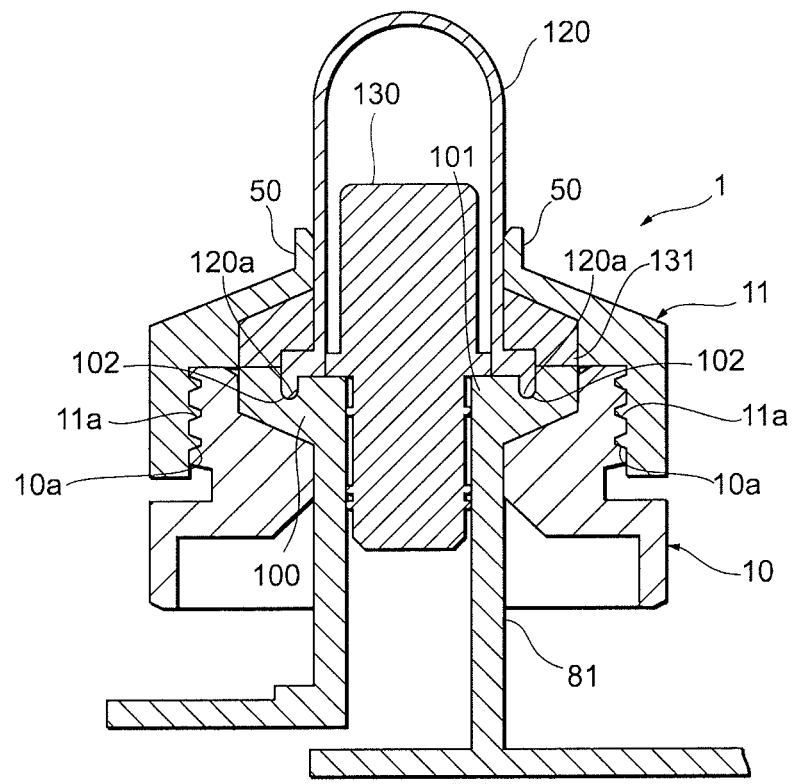
FIG. 5 is a cross-sectional view showing a sealing structure of a secondary liquid passage nozzle.

For example, as shown in FIG. 5, the secondary liquid passage nozzle 81 has a flange-shaped ferrule portion 100 at the leading end. The ferrule portion 100 has an annular flat surface 101 as the upper surface, and an annular groove 102, into which a protruding portion 120a of a closure member 120 to be described later is fitted, is formed in the flat surface 101.

Figure 6:
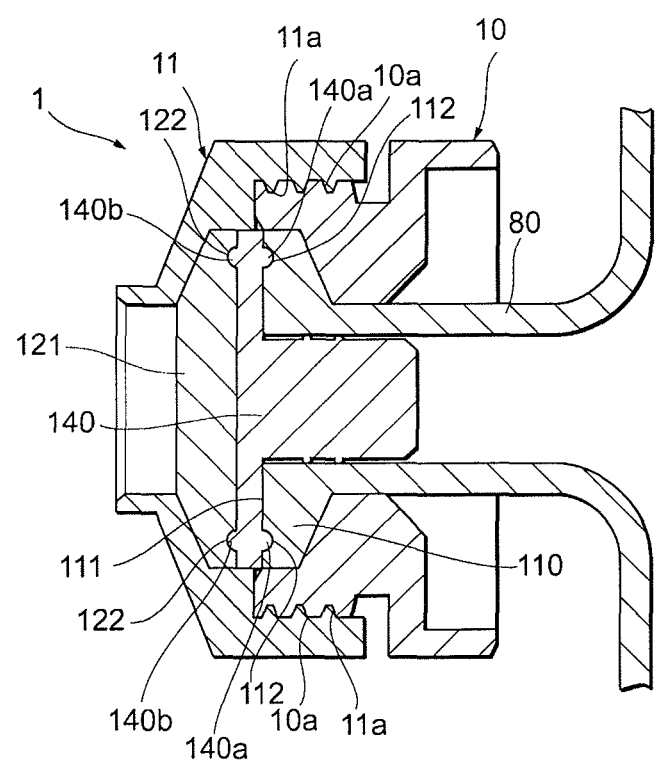
FIG. 6 is a cross-sectional view showing a sealing structure of a primary liquid passage nozzle.

For example, as shown in FIG. 6, the primary liquid passage nozzle 80 has a flange-shaped ferrule portion 110 at the leading end. The ferrule portion 110 has an annular flat surface 111 as the upper surface. An annular groove 112, into which a protruding portion 140a of, for example, a plug 140 to be described later is fitted, is formed in the flat surface 111.

The ferrule coupling 1 is used for sealing the above-described secondary liquid passage nozzles 81 and primary liquid passage nozzles 80 by means of closure members 120, 121 each serving as a member to be coupled.

As shown in FIG. 5, the closure member 120 of the secondary liquid passage nozzle 81 is, for example, a rubber balloon which can expand and contract. On the lower surface of the closure member 120, the protruding portion 120a which is fitted into the groove 102 of the ferrule portion 100 is formed. To seal the secondary liquid passage nozzle 81, the male screw member 10 of the ferrule coupling 1 is mounted on the secondary liquid passage nozzle 81, with the cut section 23 opened, while holding the secondary liquid passage nozzle 81 as one of members to be coupled. Next, a plug 130 is fitted into the secondary liquid passage nozzle 81, and the closure member 120 as the other of the members to be coupled is put over the plug 130. Next, the female screw member 11 is mounted around the closure member 120 with an annular intermediate member 131 held therebetween. Then, the male screw member 10 and the female screw member 11 are screw-engaged with each other to airtightly couple the closure member 120 and the secondary liquid passage nozzle 81 with each other.

On the other hand, as shown in FIG. 6, the closure member 121 of the primary liquid passage nozzle 80 has the shape of a circular lid. In the closure member 121, an annular groove 122, into which a protruding portion 140b of, for example, the rubber plug 140 is fitted, is formed. To seal the primary liquid passage nozzle 80, the male screw member 10 of the ferrule coupling 1 is mounted on the primary liquid passage nozzle 80, with the cut section 23 opened, while holding the primary liquid passage nozzle 80 as one of members to be coupled. Next, the plug 140 is fitted into the primary liquid passage nozzle 80, and the closure member 121 as the other of the members to be coupled is put over the plug 140. Next, the female screw member 11 is mounted around the closure member 121. Then, the male screw member 10 and the female screw member 11 are screw-engaged with each other to airtightly couple the closure member 121 and the primary liquid passage nozzle 80 with each other.

The membrane module 60 is sterilized before use with a filler liquid filling the inside and the liquid passage nozzles 80, 81 sealed. In the sterilization process, for example, the membrane module 60 is put in a sterile bag and then housed in a sterilizing chamber, and the membrane module 60 is subjected to repeated temperature rise/fall cycles in which the temperature of the sterilizing chamber is raised from room temperature to high temperature by steam, hot water, etc. In this case, since the male screw member 10 and the female screw member 11 hold the ferrule portion 110 and the closure members 120, 121 from the upper and lower sides, it is unlikely that the distance between the screw members 10, 11 changes due to temperature rises and falls, so that the sealability is maintained. Meanwhile, the filler liquid or an internal gas expands and contracts, causing the closure member 120, which is a balloon, to expand and contract. At this point, although it is expected that the balloon expands so much as to fall out of the sealing part and causes water leakage, the ridge portion 50 of the female screw member 11 functions as an expansion suppression member which suppresses expansion of the balloon from the outside.

When the membrane module 60 is used, the screw engagement between the male screw member 10 and the female screw member 11 of the ferrule coupling 1 is released in each of the liquid passage nozzles 80, 81 and the closure members 120, 121 are removed, and pipe conduits such as the tubes shown in FIG. 3 and their connector are mounted in place of the closure members 120, 121, and the male screw member 10 and the female screw member 11 are screw-engaged with each other again to couple the pipe conduits with each other.

According to this embodiment, since the male screw member 10 and the female screw member 11 of the ferrule coupling 1 are screw-engaged with each other to couple the members to be coupled with each other, and the male screw member 10 can be opened or closed such that the cut section 23 widens or narrows, the work of coupling the members to be coupled with each other by means of the ferrule coupling 1 requires no practice and skills, and high sealability can be reliably maintained even when the ferrule coupling is subjected to large temperature rises and falls. Even if tightening between the male screw member 10 and the female screw member 11 should loosen, these screw members can be fastened again. In particular, the conventional clamp band cannot be fastened again once a filter is put in a sterile bag and the bag is sealed before the sterilization process, since the binding band cannot be pulled over the sterile bag. By contrast, the ferrule coupling 1 of this embodiment can be fastened again even over a sterile bag. Thus, the sealability after the sterilization process can be secured reliably. Moreover, to remove the conventional clamp band, one needs to bring a knife into a clean room and cut the clamp band, while one can easily remove the ferrule coupling 1 of this embodiment by hand without the need for bringing a knife into a clean room.

Since the male screw member 10 is divided into two arc members 20, 21 and the arc members 20, 21 are connected with each other through the connection member 22 except at the one part defining the cut section 23, the male screw member 10 can be opened and closed with a simple configuration. Moreover, as the allowance for the inner diameter of the male screw member 10 increases and the range of the outer diameter of members to be coupled which can be held in the male screw member 10 increases, it becomes easier to deal with members to be coupled having various outer diameters. While the male screw member in this embodiment is divided into two arc members, it may be divided into three or more arc members.

Since the connection member 22 has higher flexibility than the arc members 20, 21, it can favorably open and close the male screw member 10. Moreover, the range of the outer diameter of members to be coupled on which the male screw member 10 can be mounted further widens. The flexibility of the connection member 22 may be realized through the shape or the material. For example, to realize the flexibility through the shape, the connection member may have an elongated shape, a wave shape, a coil-like shape, etc., and to realize the flexibility through the material, the connection member may be made of a soft resin.

Since the male screw member 10 and the female screw member 11 have the handhold parts 30, 51 having the plurality of protrusions 30a, 51a projecting radially outwardly, it is possible to easily tighten the male screw member 10 and the female screw member 11 with each other and to secure higher sealability. Alternatively, only one of the male screw member 10 and the female screw member 11 may have the handhold part.

According to this embodiment, since the sealing structure of the liquid passage nozzles 80, 81 of the membrane module 60 is realized by the male screw member 10 and the female screw member 11 of the ferrule coupling 1 airtightly coupling the liquid passage nozzles 80, 81 and the closure members 120, 121 with each other, the work of closing the liquid passage nozzles 80, 81 is easy and does not require practice and skills, and high sealability can be reliably maintained even when the ferrule coupling 1 is subjected to large temperature rises and falls during the sterilization process before use.

Since the closure member 120 is a balloon which is airtightly mounted on the secondary liquid passage nozzle 81 of the membrane module 60 and can expand and contract, high sealability between the balloon and the secondary liquid passage nozzle 81 can be maintained.

Since the ridge portion 50 serving as the expansion suppression member is formed in the female screw member 11, it is possible to suppress expansion of the balloon during the sterilization process and to thereby further improve the sealability of the secondary liquid passage nozzle 81.

Figure 7A:
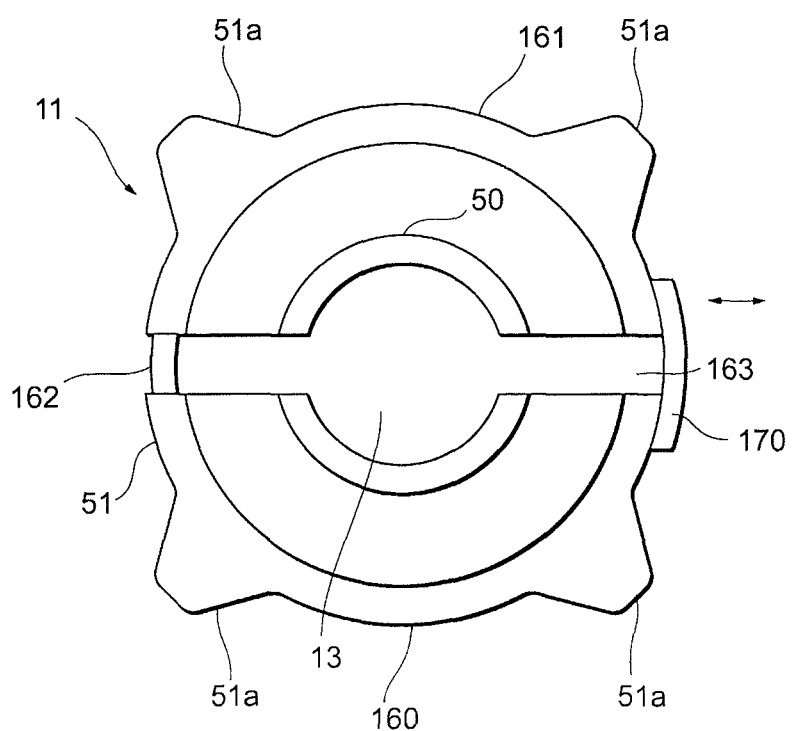
FIG. 7A is a plan view of a female screw member which can be opened and closed.
Figure 7B:
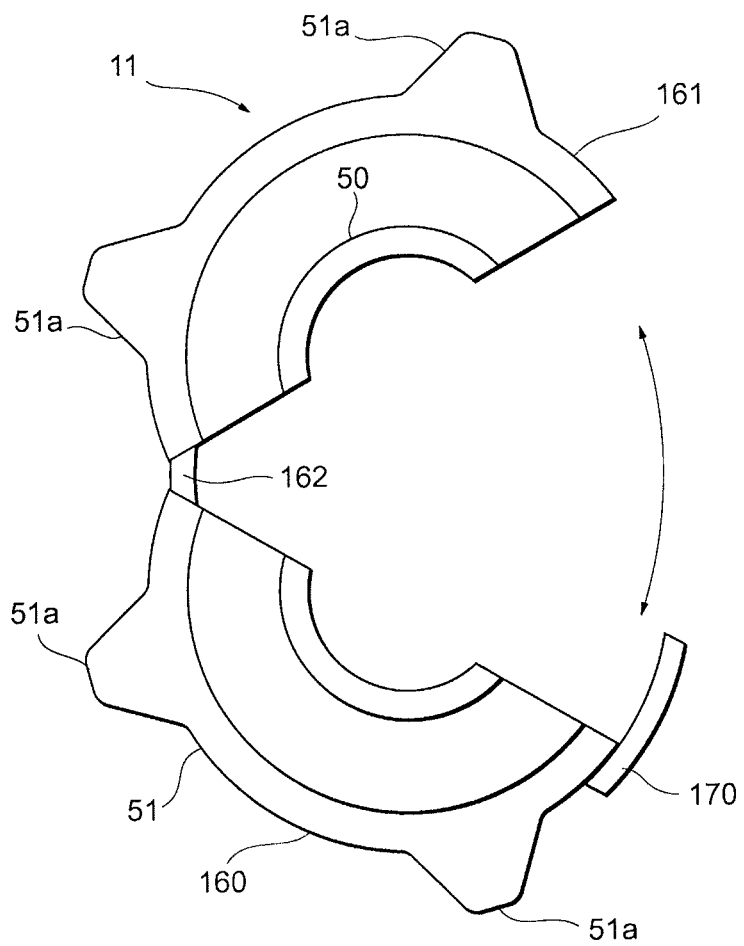
FIG. 7B is a plan view showing the female screw member in its open state.

In the above embodiment, the female screw member 11 may also be able to be opened and closed as with the male screw member 10. In this case, for example, the female screw member 11 is divided into a plurality of, for example, two arc members 160, 161 as shown in FIG. 7A and FIG. 7B. One ends in the circumferential direction of the arc members 160, 161 are connected with each other through a connection member 162, while the other ends define a cut section 163. The connection member 162 has higher flexibility than the arc members 160, 161. The connection member 162 connects, for example, outermost peripheral portions in the circumferential direction of the ends of the arc members 160, 161. The female screw member 11 can be opened or closed by the cut section 163 widening or narrowing with the connection member 162 serving as the fulcrum.

Figure 8:
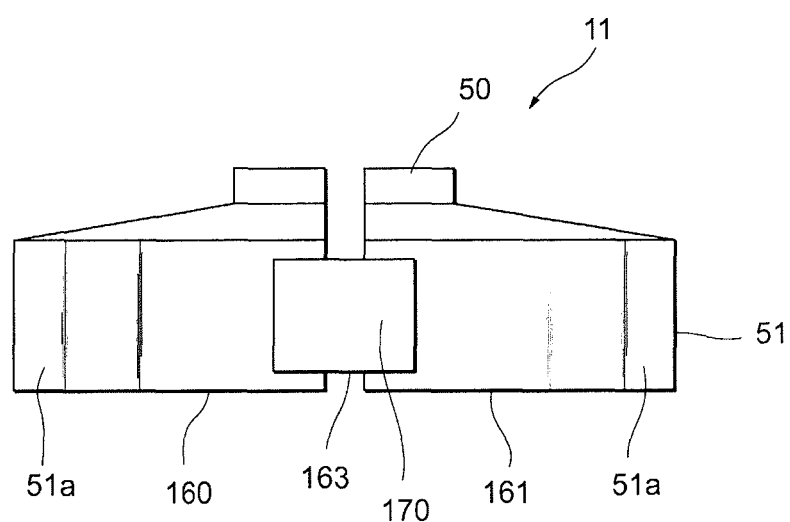
FIG. 8 is a side view of the female screw member.

As shown in FIG. 7A and FIG. 8, the female screw member 11 is provided with an opening regulation member 170 which can regulate the opening of the female screw member 11. The opening regulation member 170 has the shape of a thin band, and, for example, has one end connected at the end in the circumferential direction of the arc member 160 on the cut section 163 side, while the other end can be attached on and detached from the end in the circumferential direction of the arc member 161. To use this female screw member 11, the opening regulation member 170 is released and the female screw member 11 is mounted on the outer periphery of the closure members 120, 121 with the cut section 163 opened, and then the opening of the female screw member 11 is regulated by the opening regulation member 170. Then, the female screw member 11 and the male screw member 10 are screw-engaged with each other to couple the closure members 120, 121 and the liquid passage nozzles 81, 80 with each other. The opening regulation member 170 may have a different structure; for example, the leading end of the opening regulation member 170 may be inserted into the arc member 161 so that the opening regulation member 170 can be attached on or detached from the arc member 161.

According to this example, since the female screw member 11, in addition to the male screw member 10, can be opened and closed, the work of mounting the male screw member 10 and the female screw member 11 onto members to be coupled is further simplified.

Since the female screw member 11 is divided into the two arc members 160, 161, and these arc members 160, 161 are connected with each other through the connection member 162 except at the one part defining the cut section 163, the female screw member 11 can be opened and closed with a simple configuration. Moreover, as the allowance for the outer diameter of members to be coupled increases, it becomes easier to deal with members to be coupled having various outer diameters. While the female screw member 11 in this embodiment is divided into two arc members, it may be divided into three or more arc members.

Since the connection member 162 has higher flexibility than the arc members 160, 161, it can favorably open and close the female screw member 11. Moreover, the range of the outer diameter of members to be coupled on which the female screw member 11 can be mounted widens. In particular, since both of the male screw member 10 and the female screw member 11 can be opened and closed, the range of the outer diameter of members to be coupled on which these screw members can be mounted significantly widens. The flexibility of the connection member 162 may be realized through the shape or the material. For example, to realize the flexibility through the shape, the connection member may have a wave shape, a coil-like shape, etc., and to realize the flexibility through the material, the connection member may be made of a soft resin.

Figure 9:
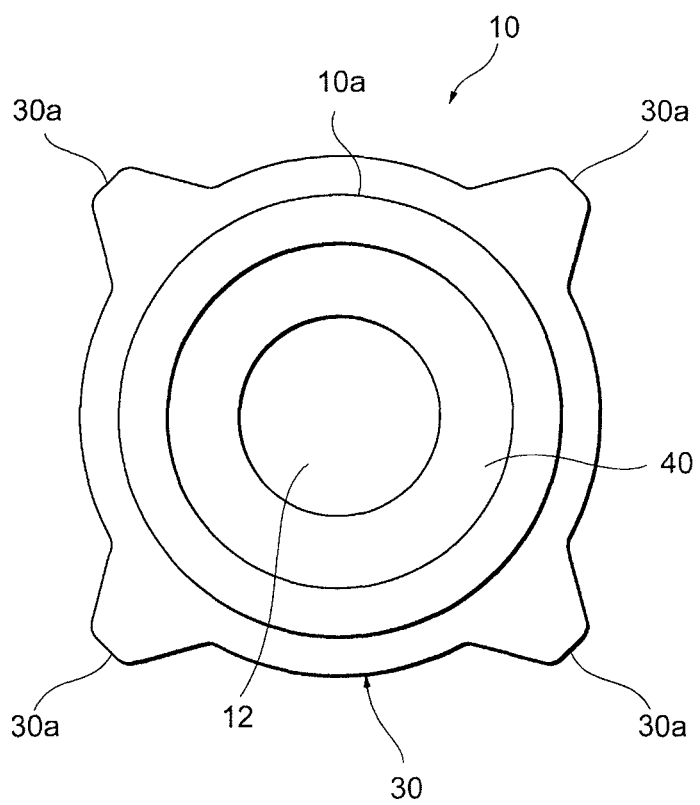
FIG. 9 is a plan view of a male screw member which is not opened or closed.

In the above embodiment, it may be only the female screw member 11 that can be opened and closed. In this case, as shown in FIG. 9, the male screw member 10 may have an annular shape without the cut section. In this case, too, as with the above embodiment, after the male screw member 10 is mounted on each of the liquid passage nozzles 80, 81, the opening regulation member 170 of the female screw member 11 is released, and the female screw member 11 is mounted on the outer periphery of the closure members 120, 121 with the cut section 163 opened, and then the opening of the female screw member 11 is regulated by the opening regulation member 170. Then, the female screw member 11 and the male screw member 10 are screw-engaged with each other to couple the closure members 120, 121 and the liquid passage nozzles 81, 80 with each other.

While the preferred embodiment of the present invention has been described with reference to the accompanying drawings, the present invention is not limited to this example. It is obvious to those skilled in the art that various altered examples or modified examples are conceivable within the scope of the concept described in the claims, and it is understood that such examples also belong naturally to the technical scope of the present invention.

For example, in the above-described embodiment, the male screw member 10 is mounted on the liquid passage nozzles 80, 81 and the female screw member 11 is mounted on the closure members 120, 121, but this may be vice versa. It is not absolutely necessary to use the ferrule coupling 1 for all the four liquid passage nozzles of the membrane module 60, and instead the ferrule coupling 1 may be used for only some of the liquid passage nozzles. The configurations of the male screw member 10 and the female screw member 11 are not limited to those of the above-described embodiment, and the male screw member 10 and the female screw member 11 may have other configurations. The intended purpose of the ferrule coupling 1 according to the present invention is not limited to coupling of the liquid passage nozzle of the membrane module 60, and the ferrule coupling 1 may be used for other coupling portions of processing circuits having the membrane module 60. The ferrule coupling 1 may also be used for other coupling portions of other pipe conduits, apparatuses, and devices in the medical field which have no membrane module 60. The present invention can also be applied to coupling of pipe conduits, apparatuses, and devices having a ferrule in the fields of pharmaceuticals and food other than the medical field. Moreover, the present invention can be applied to two members to be coupled, at least one of which has a ferrule.

EXAMPLE

Of 12 samples of membrane modules, the liquid passage nozzles were closed using the ferrule coupling 1 according to the present invention and a conventional clamp joint (similar to that of Patent Literature 1), and after three times of a sterilization process, a vacuum leak test and a pressure test were performed. In these tests, membrane modules 300 mm in overall length and 72.5 mm in diameter were used. The sterilization process was performed at 121° C. for 110 minutes using a high-pressure steam sterilization machine. In the vacuum leak test, the membrane modules after sterilization were placed in a vacuum dryer and checked for water leakage at 3 kPa or less. In the pressure test (pressurization test), the membrane modules were checked for water leakage while pressures ranging from 100 to 500 kPa were applied to the membrane modules using a hydraulic test machine. The results of these tests are shown in Table 1 of FIG. 11. The results of these tests confirmed that, when the ferrule coupling 1 according to the present invention was used, the sealability after the sterilization process was reliably maintained.

REFERENCE SIGNS LIST

1 Ferrule coupling
10 Male screw member
10a Thread
11 Female screw member
11a Thread
20, 21 Arc member
22 Connection member
23 Cut section
60 Membrane module
80 Primary liquid passage nozzle
81 Secondary liquid passage nozzle
100, 110 Ferrule portion
120, 121 Closure member

The invention claimed is:

1. A ferrule coupling used in the field of manufacturing of pharmaceutical and medical products or food manufacturing, the ferrule coupling comprising:
    an annular male screw member which can be fitted on one member that is to be coupled to another member, the male screw member having a thread formed on an outer peripheral surface thereof; and
    an annular female screw member which can be fitted on the another member, the female screw member having a thread formed on an inner peripheral surface thereof, wherein
    the male screw member and the female screw member are screw-engaged with each other to thereby couple the one member and the another member with each other,
    the male screw member has a cut section at only one part in a circumferential direction thereof, and can be opened or closed such that the cut section widens or narrows, the male screw member is divided into a plurality of arc members, and
        the plurality of arc members are spaced apart from one another at respective divided surfaces when fitted on the one member, wherein
    the plurality of arc members are connected with one another through a connection member except at the one part defining the cut section.

2. The ferrule coupling according to claim 1, wherein
    the female screw member has a cut section at one part in a circumferential direction thereof, and can be opened or closed such that the cut section widens or narrows, and
    the ferrule coupling further comprises an opening regulation member which can regulate the opening of the female screw member.

3. The ferrule coupling according to claim 1, wherein the connection member has higher flexibility than the arc member.

4. A ferrule coupling used in the field of manufacturing of pharmaceutical and medical products or food manufacturing, the ferrule coupling comprising:
- an annular male screw member which can be fitted on one member that is to be coupled to another member, the male screw member having a thread formed on an outer peripheral surface thereof; and
- an annular female screw member which can be fitted on the another member, the female screw member having a thread formed on an inner peripheral surface thereof, wherein
- the male screw member and the female screw member are screw-engaged with each other to thereby couple the one member and the another member to be coupled with each other,
- the female screw member has a cut section at only one part in a circumferential direction thereof, and can be opened or closed such that the cut section widens or narrows,
- the ferrule coupling further comprises an opening regulation member which can regulate the opening of the female screw member,
- the female screw member is divided into a plurality of arc members, and
- the plurality of arc members are spaced apart from one another at respective divided surfaces when fitted on the another member, wherein
- the plurality of arc members are connected with one another through a connection member except at the one part defining the cut section.

5. The ferrule coupling according to claim 1 or claim 4, wherein at least one of the male screw member and the female screw member has a handhold part having a plurality of protrusions projecting radially outwardly.

6. The ferrule coupling according to claim 1 or claim 4, wherein the male screw member has, in the inner peripheral surface, a recessed portion which houses the end of the one member.

7. The ferrule coupling according to claim 6, wherein the recessed portion of the male screw member is formed so as to match the shape of the end of the one member.

8. The ferrule coupling according to claim 1 or claim 4, wherein the female screw member has, in the inner peripheral surface, a recessed portion which houses the end of the another member.

9. The ferrule coupling according to claim 8, wherein the recessed portion of the female screw member is formed so as to match the shape of the end of the another member.

10. The ferrule coupling according to claim 1 or claim 4, which couples the one member and the another member with each other via a flange-shaped ferrule portion at an end of each of the one member and the another member.

11. The ferrule coupling according to claim 4, wherein the connection member has higher flexibility than the arc member.

12. A sealing mechanism for a liquid passage nozzle of a membrane module comprising the ferrule coupling according to claim 1 or claim 4, wherein the male screw member and the female screw member of the ferrule coupling are screw-engaged with each other to thereby airtightly couple a liquid passage nozzle of a membrane module and a closure member which closes the liquid passage nozzle with each other.

13. The sealing mechanism for a liquid passage nozzle of a membrane module according to claim 12, wherein the closure member is a balloon which is airtightly coupled on the liquid passage nozzle of the membrane module and can expand and contract.

14. The sealing mechanism for a liquid passage nozzle of a membrane module according to claim 13, wherein the male screw member or the female screw member provided on the balloon side is provided with an expansion suppression member which suppresses expansion of the balloon.

* * * * *